United States Patent
Weber et al.

(10) Patent No.: US 9,554,823 B2
(45) Date of Patent: Jan. 31, 2017

(54) VIBRATION AND INERTIA ENHANCED ATHERECTOMY

(71) Applicant: BOSTON SCIENTIFIC SCIMED, INC., Maple Grove, MN (US)

(72) Inventors: Jan Weber, Maastricht (NL); James M. Anderson, Fridley, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 262 days.

(21) Appl. No.: 14/192,562

(22) Filed: Feb. 27, 2014

(65) Prior Publication Data

US 2014/0277010 A1 Sep. 18, 2014

Related U.S. Application Data

(60) Provisional application No. 61/777,776, filed on Mar. 12, 2013.

(51) Int. Cl.
*A61B 17/22* (2006.01)
*A61B 17/3207* (2006.01)
*A61B 17/00* (2006.01)
*A61B 17/32* (2006.01)

(52) U.S. Cl.
CPC ............... *A61B 17/320758* (2013.01); *A61B 17/320725* (2013.01); *A61B 2017/00862* (2013.01); *A61B 2017/320004* (2013.01); *A61B 2017/320766* (2013.01)

(58) Field of Classification Search
CPC ............ A61B 17/22; A61B 17/320758; A61B 17/3207; A61B 17/320733; A61B 5/00; A61B 17/50; A61B 17/3421
See application file for complete search history.

(56) References Cited

U.S. PATENT DOCUMENTS

| | | | |
|---|---|---|---|
| 2,261,230 A | * | 11/1941 | Cox ............... A61B 17/14 30/500 |
| 5,632,755 A | | 5/1997 | Nordgren et al. |
| 5,681,336 A | | 10/1997 | Clement et al. |
| 5,746,758 A | | 5/1998 | Nordgren et al. |
| 5,836,868 A | | 11/1998 | Ressemann et al. |

(Continued)

FOREIGN PATENT DOCUMENTS

| | | |
|---|---|---|
| JP | 2004508096 A | 3/2004 |
| WO | 0024321 A2 | 5/2000 |

OTHER PUBLICATIONS

"Diamondback 360® Orbital Atherectomy Device, Solid Crown, 30 µm, with 15 cm Travel" 2011, Cardiovascular Systems, Inc. Instructions Manual, p. 1-17.

*Primary Examiner* — Victor Nguyen
(74) *Attorney, Agent, or Firm* — Seager, Tufte & Wickhem, LLP

(57) ABSTRACT

An atherectomy device is disclosed herein. The atherectomy device includes a first drive shaft, a second drive shaft, a handle assembly, and a cutting member. The first drive shaft extends distally from the handle assembly and includes the cutting member mounted on a distal end region of the first drive shaft. The second drive shaft extends distally from the handle assembly to a distal end of the second drive shaft such that both the first and the second drive shafts are rotatable relative to the handle assembly, and the first drive shaft is rotatable independent of the second drive shaft.

15 Claims, 8 Drawing Sheets

(56) References Cited

U.S. PATENT DOCUMENTS

| | | | |
|---|---|---|---|
| 6,146,395 A | 11/2000 | Kanz et al. | |
| 6,494,890 B1 | 12/2002 | Shturman et al. | |
| 7,628,763 B2 * | 12/2009 | Noriega | A61B 17/320758 |
| | | | 600/585 |
| 8,043,312 B2 | 10/2011 | Noriega et al. | |
| 8,579,926 B2 | 11/2013 | Pintor et al. | |
| 2005/0228418 A1 | 10/2005 | Noriega et al. | |
| 2009/0105736 A1 | 4/2009 | Prudnikov et al. | |
| 2009/0264908 A1 | 10/2009 | Kallok et al. | |
| 2010/0121361 A1 | 5/2010 | Plowe et al. | |
| 2010/0198239 A1 | 8/2010 | McBroom et al. | |
| 2012/0046600 A1 | 2/2012 | Kohler et al. | |

* cited by examiner

VIBRATION AND INERTIA ENHANCED ATHERECTOMY

CROSS-REFERENCE TO RELATED APPLICATIONS

This application claims priority under 35 U.S.C. §119 to U.S. Provisional Application Ser. No. 61/777,776, filed Mar. 12, 2013, the entirety of which is incorporated herein by reference.

TECHNICAL FIELD

The present disclosure relates generally to devices and methods for performing atherectomy of an occluded blood vessel. More particularly, the technologies disclosed herein relate to devices and methods for a vibration and inertia enhanced atherectomy.

BACKGROUND

Occlusions, such as chronic total occlusions (CTO), are arterial vessel blockages that obstruct blood flow through a vessel. A diseased condition called arthrosclerosis generally results in formation of an occlusion, which can occur in both coronary and peripheral arteries. In general, a minimally invasive procedure called atherectomy may be employed to treat such vessel occlusions. Atherectomy procedures may include the use of rotational, orbital, laser, and/or directional atherectomy devices, for example.

A typical rotational atherectomy device includes a shaft having a cutting member disposed at its distal end. The cutting member is rotated via a drive shaft coupled to a handle assembly while being advanced inside the vessel to penetrate through the occlusion. The rotating cutting member thus forms an opening while penetrating through the occlusion. In general, the opening formed may have dimensions either equal to or slightly larger than the dimensions of the cutting member. Thus, a larger cutting member must be provided to form a larger opening through the occlusion, adversely impacting the ability to navigate the cutting member through the vasculature.

In some instances, it may be desirable to form an opening significantly larger than the original dimensions of the cutting member in some instances. Accordingly, a need remains to use smaller profile cutting members, which may facilitate navigation through the vasculature to an occlusion, yet are configured to create a larger passage through the occlusion.

SUMMARY

The disclosure is directed to several alternative designs, and methods of using medical device structures and assemblies for performing atherectomy of occluded blood vessels.

Accordingly, one illustrative embodiment includes an atherectomy device having a first drive shaft, a second drive shaft, a handle assembly, and a cutting member. The first drive shaft extends distally from the handle assembly and includes the cutting member mounted on a distal end region of the first drive shaft. The second drive shaft also extends distally from the handle assembly to a distal end of the second drive shaft. It is contemplated that the first and the second drive shafts are independently rotatable relative to the handle assemble.

Another illustrative embodiment of an atherectomy device includes a handle assembly, a rotatable drive shaft, a cutting member, and a weight. The rotatable drive shaft extends distally from the handle assembly and rotatable relative to the handle assembly about a rotational axis. The cutting member is formed of an elastically deformable material that is disposed on a distal end portion of the rotatable drive shaft. The weight is positioned with the cutting member and has a center of mass eccentrically located relative to the rotational axis. The rotatable drive shaft is configured to rotate at a rotational rate that is above a threshold rotational rate providing centrifugal forces to act on the weight, which causes the cutting member to deform radially outward from the rotational axis.

Yet another illustrative embodiment includes a method of forming an opening through an occlusion in a blood vessel using a rotational atherectomy device. The method includes advancing a cutting member of a rotatable cutting device to a location proximate an occlusion while the cutting member is mounted to a first drive shaft of the rotatable cutting device. Further, the method includes rotating the first drive shaft while advancing the cutting member through the occlusion. Still further, the method includes rotating a second drive shaft of the rotatable cutting device to initiate vibration of the cutting member while advancing the cutting member through the occlusion.

The above summary of some example embodiments is not intended to describe each disclosed embodiment or every implementation of the present disclosure.

BRIEF DESCRIPTION OF THE DRAWINGS

The disclosure may be more completely understood in consideration of the following detailed description of various embodiments in connection with the accompanying drawings, in which.

Figure 1:
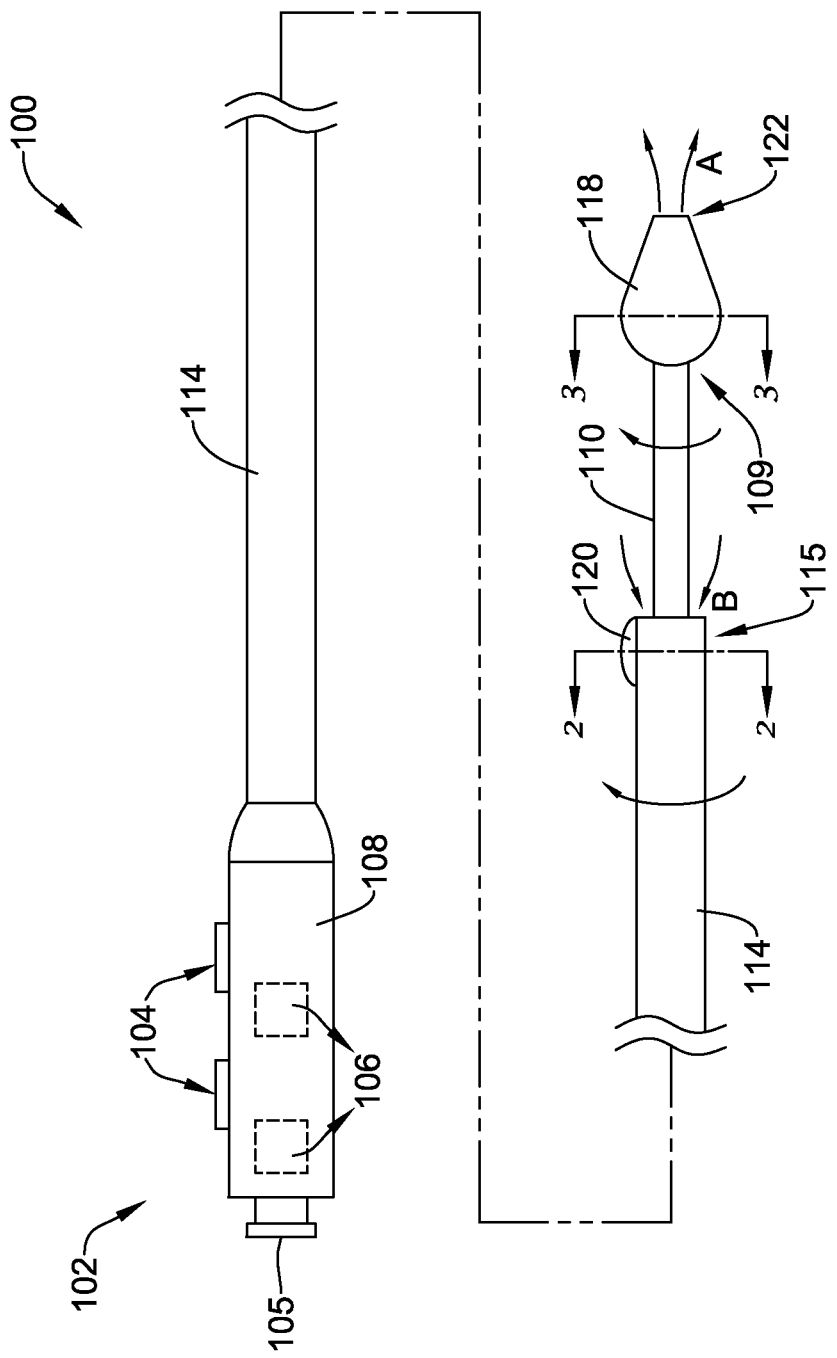
FIG. 1 is a side view of an exemplary atherectomy device according to the present disclosure.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification. All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

While the devices and methods described herein are discussed relative to canalization of a blood vessel to pass through an occlusion, such as chronic total occlusions (CTO), it is contemplated that the devices and methods may be used in other applications as desired. In addition, embodiments of the present disclosure include by way of an example a rotational atherectomy device adapted for channelization or revascularization of an occluded blood vessel. It will be understood however that the present disclosure may also be implemented for other suitable atherectomy techniques such as, but not limited to, orbital, directional, and/or laser atherectomy.

The present disclosure provides methods and devices for revascularization of an occluded blood vessel. In an embodiment, the device includes an atherectomy device having a first rotatable drive shaft operably and rotatably connected to a handle assembly at a proximal end region. The first rotatable drive shaft includes a cutting member disposed at a distal end region of the drive shaft. Further, in some instances the atherectomy device may also include a second drive shaft having an eccentric weight disposed on its distal end region. A proximal end of the second drive shaft may be operably and rotatably coupled to the handle assembly, which is configured to rotate the second drive shaft independent to the rotation of the first drive shaft. It is contemplated that the rotation of the second drive shaft above a threshold rotational rate may generate a vibration of the first drive shaft, which may further allow vibration of the cutting member. Thus, the vibration and rotation of the cutting member may provide canalization of the blood vessel by forming an opening through an occlusion having a size (e.g., diameter) notably larger than the size (e.g., diameter) of the cutting member.

In the following sections, a variety of exemplary structural and functional features of atherectomy devices will be described. It will be understood that the components and the configurations of the atherectomy device are just exemplary and thus not limiting the scope and spirit of the present disclosure.

Exemplary Embodiments

FIG. 1 is a side view of an exemplary atherectomy device 100 for revascularization of an occluded blood vessel. In the illustrated embodiment, the atherectomy device 100 along with other components includes a handle assembly 102, a first drive shaft 110, a second drive shaft 114, a cutting member 118, and an eccentrically positioned weight 120. Components of the atherectomy device 100 will now be discussed in detail.

The first drive shaft 110 may be an elongated body having a proximal end region proximate the handle assembly 102, a distal end region 109, and a lumen 111 (see FIGS. 2 and 3) extending between the proximal and distal end regions. In some embodiments the first drive shaft 110 may be a solid member, while in other embodiments the first drive shaft 110 may be a tubular body having a lumen 111 extending therethrough. In one embodiment, the first drive shaft 110 may be configured to extend distally within a body cavity (not shown) to a target location (e.g., an occlusion) while the proximal end region may remain external to a patient's body. Further, the proximal end region of the first drive shaft 110 may be operably coupled to a handle assembly 102. The handle assembly 102 may be configured to rotate the first drive shaft 110 at a desired rotational rate, and will be described in detail hereinafter. In some instances the rotational rate of the first drive shaft 110 may be fixed or variable, as desired.

Further, the second drive shaft 114 may also be operably coupled to the handle assembly 102. As shown, the second drive shaft 114 may define an elongated tubular body having a distal end region 115 configured to extend within a body cavity. In addition, the second drive shaft 114 may define a lumen 117 (see FIG. 2) that may substantially encompass at least a portion of the first drive shaft 110. As shown, the inner, first drive shaft 110 may extend through the lumen 117 of the outer, second drive shaft 114 with the cutting member 118 positioned distal of the second drive shaft 114. As a result, the distal end region 109 of the first drive shaft 110 may extend distally from the distal end region 115 of the second drive shaft 114. The handle assembly 102 may be configured to rotate the second drive shaft 114 at a desired rotational rate, independent of the first drive shaft 110. In some instances, the rotational rate of the second drive shaft 114 may be fixed or variable, as desired.

As shown, the first and the second drive shafts (110, 114) may be configured with a substantially circular cross-section, although other suitable cross-sectional shapes of the two drive shafts (110, 114) may be employed, such as elliptical, oval, polygonal, irregular, etc. In addition, the two drive shafts (110, 114) may be flexible along their entire length or adapted for flexure along portions of their length. The required degree of flexibility of each of the two drive shafts (110, 114) may be predetermined based on its intended navigation to a target vascular passage and/or the amount of force required for advancing the two drive shafts (110, 114) through the vascular passage. The cross-sectional dimensions of the two drive shafts (110, 114) may vary according to the desired application. Generally, the cross-sectional dimensions of the drive shafts (110, 114) are smaller than the typical diameter of the blood vessel lumen in locations where the atherectomy device 100 is to be used such as in a coronary artery or in a peripheral vasculature. The length of the two drive shafts (110, 114) may vary according to the location of the vascular passage where revascularization is to be conducted. In addition, the two drive shafts (110, 114) or a portion thereof may be selectively steerable. Mechanisms such as, pull wires, motors, hydraulics or other actuators may be used to selectively steer the two drive shafts (110, 114), if desired.

The two drive shafts (110, 114) may include one or more proximal ports, which may be located anywhere along the length of the drive shafts (110, 114) and/or the handle assembly 102. Such ports may be used to introduce a guidewire (not shown) into the drive shafts (110, 114) to facilitate advancing the cutting member 118 to a target location. It will be understood that the drive shafts (110, 114) may be further adapted to include more openings or lumens, which may be configured for a variety of purposes such as delivering medical devices or for providing fluids, such as saline, to a target location.

In one embodiment, the two shafts (110, 114) may be either detachably connected or permanently coupled to the handle assembly 102. The two drive shafts (110, 114) may be coupled to a distal end of handle assembly 102 by any suitable coupling mechanism capable of achieving the intended purpose in the intended environment.

Further, the handle assembly 102 may include one or more components. For example, the handle assembly 102 may include an ergonomically designed handle 108 to provide a comfortable grip on the atherectomy device 100 during operation, and one or more actuators 104 to control its operation. For example, the handle assembly 102 may include a first actuator 104 to control starting and/or stopping rotation, the speed of rotation, and/or the direction of rotation, of the first drive shaft 110. The handle assembly 102 may also include a motor assembly 106 configured to operate the first drive shaft 110 and/or the second drive shaft 114. As shown in the illustrative embodiment, the handle assembly 102 may include a first motor assembly 106 coupled to the first drive shaft 110 to provide rotational movement to the first drive shaft 110 and a second motor assembly 106 coupled to the second drive shaft 114 to provide rotational movement to the second drive shaft 114. However, in other embodiments the two drive shafts (110, 114) may also be operated using a single motor 106, if desired. In the present disclosure, the "motor" may be an electric motor, a pneumatic motor, or any suitable device that generates a controllable amount of rotation. The handle assembly 102 may include one or more ports or openings 105 for a variety of purposes, for example, to facilitate insertion of a guidewire, to insert a variety of other medical devices, to deliver fluid to a target location and/or aspirate fluid from a target location, etc. For example, the handle assembly 102 may include a fluid port (e.g., a fluid inlet or outlet) in fluid communication with the lumen 111, a fluid port (e.g., a fluid outlet or inlet) in fluid communication with the lumen 117, and a guidewire port for passage of a guidewire therethrough.

The handle assembly 102 may further include a clutch mechanism mechanically coupling the first and/or second drive shafts (110, 114) to the motor assembly 106 of the handle assembly 102. It may be contemplated that a single motor 106 may be employed to rotate both of the drive shafts (110, 114), in which case a clutch mechanism may be utilized to independently and selectively control rotation of the second drive shaft 114 relative to the first drive shaft 110. More particularly, the clutch may be configured to selectively engage the second drive shaft 114 to the motor 106, and thus selectively engage rotation of the second drive shaft 114 and disengage rotation of the second drive shaft 114 while the first drive shaft 110 may continue to be engaged and rotated by the motor 106. In some instances, the first drive shaft 110 may be directly driven by the motor 106 when the motor 106 is turned on, or a clutch mechanism may also be employed to control engagement/disengagement of the first drive shaft 110 with the motor 106. During use, the clutch may be engaged with the drive shaft(s) (110, 114), which may pass the rotational movement produced by the motor(s) 106 directly to the drive shaft(s) (110, 114). Additionally, the clutch may provide a convenient interface between the drive shafts (110, 114), which may be a replaceable or disposable element, and the motor 106, which may be used repeatedly. The clutch mechanism may, for example, be a magnetic clutch, a hydro-fluid clutch, an electronic clutch, a mechanical clutch or other clutch mechanism, as desired.

Further, the cutting member 118 may be disposed adjacent the distal end region 109 of the first drive shaft 110 such that the cutting member 118 may be positioned distal to the distal end region 115 of the second drive shaft 114. More particularly, the cutting member 118 may be mounted on the distal end region 109 while being concentric to the first drive shaft 110. In contrast, the cutting member 118 may also be mounted on the distal end region 109 while being eccentric to the first drive shaft 110. In either case, the cutting member 118 may have a uniform weight density around its central axis. Therefore, rotation of the cutting member 118 at a pre-determined rotational rate may form an opening having an outer diameter equal to the outer diameter of the cutting member 118.

Still further, the cutting member 118 may include an aperture 122 that may remain in fluid communication with the lumen 111 of the first drive shaft 114 and having access to the surrounding environment. The lumen 111 in conjunction with the aperture 122 may be configured to deliver a fluid, a device, or other interventions to the surrounding environment (for example, the blood vessel). For instance, an aspiration fluid may be delivered to the cutting member 118 to flush debris from the target location, a coolant may be delivered to the blood vessel that may compensate for the heat generated during an artherectomy procedure, and/or a variety of drugs may be delivered through the aperture 122 providing a therapy. Those skilled in the art will appreciate that the aperture 122 may be used to deliver a device such as a guide wire, or the like within the body cavity through the lumen 111.

As discussed previously, the cutting member 118 may include any suitable device configured to revascularize an occluded blood vessel. Exemplary cutting members may include, but are not limited to, a burr, drill bit, blade, fluted cutter, or the like. In addition, the cutting member 118 may be made from a suitable material such as, but not limited to, metals, alloys, polymers, ceramics, composites, or the like capable of cutting the occlusion or other material. In some embodiments, the cutting member 118 may be coated with suitable abrasive materials. The abrasive material may be any suitable material, such as diamond powder, fused silica, titanium nitride, tungsten carbide, aluminum oxide, boron carbide, or other ceramic materials. Preferably the abrasive material is comprised of diamond chips (or diamond dust particles) attached directly to the cutting member 118 by a suitable binder. Such binding may be achieved using well known techniques, such as conventional electroplating or fusion technologies (see, e.g., U.S. Pat. No. 4,018,576). Alternatively, the external surface of the cutting member 118 may include a section that has been roughened to provide a suitable abrasive surface. In yet another variation, the external surface of the cutting member 118 may be etched or cut (e.g., with a laser) to provide small but sharp cutting surfaces. Other similar techniques may also be utilized to provide a suitable abrasive surface.

Further, the eccentric weight 120 may be disposed adjacent the distal end region 115 of the second drive shaft 114 and secured thereto. In other embodiments, the eccentric weight 120 may be formed as an integral or monolithic portion of the second drive shaft 114. In one embodiment, the eccentric weight 120 may include an oval-shaped mass disposed around a portion of an outer surface of the distal end region 115. In other embodiments, the eccentric weight 120 may surround the second drive shaft 114 and be asymmetrically distributed around the rotational axis of the second drive shaft 114. Other suitable shapes of the eccentric weight 120 may also be contemplated. Exemplary shapes may include circular, rectangular, polygonal, irregular, or the like. In one embodiment, the eccentric weight 120 may be made from a suitable material such as, but not limited to, metals, alloys, polymers, ceramics, composites, or the like. It is to be noted that the materials and shapes of the eccentric weight 120 are presented here as examples and thus not intended to limit the scope of the present disclosure.

In one embodiment, the atherectomy device 100 may be used for revascularization of an occluded blood vessel. To accomplish this, the cutting member 118, disposed at the distal end of the first drive shaft 110, may be placed adjacent the occlusion inside the blood vessel, which may be configured to rotate at a desired rotational rate. Further, the eccentric weight 120, disposed at the distal end of the second drive shaft 114, may be configured to be selectively rotated at a desired rotational rate to cause the first drive shaft 110 to vibrate. Therefore, the cutting member 118 may also be vibrated allowing the cutting member 118 to form an opening with a larger diameter as compared to the diameter of the cutting member 118. In such instances, the atherectomy device 100 may provide larger canalization through an occlusion than the actual size of the cutting member 118. In other words, the cutting member 118 may form an opening having a diameter notably greater than the diameter of the cutting member 118.

In some embodiments, the first drive shaft 110 and cutting member 118 may be configured to be rotated in the same direction as the second drive shaft 114 and eccentric weight 120, while in other embodiments the first drive shaft 110 and cutting member 118 may be configured to be rotated in a first direction, while the second drive shaft 114 and eccentric weight 120 may be rotated in a second direction, opposite the first direction. In some embodiments, the first drive shaft 110 may be configured to be selectively rotated in either direction and/or the second drive shaft 114 may be configured to be selectively rotated in either direction. Rotating the second drive shaft 114 in the opposite direction as the first drive shaft 110 may help maintain the angular moment to zero, which may be useful to bend the device around corners while rotating the first drive shaft 110 at high speeds without the cutting member 118 starting a precession. Thus, in a configuration having first and second drive shafts 110, 114 including weighted elements at the distal ends thereof, rotating in opposite directions, the angular momentum of each weighted element may be equal in absolute magnitude to the other weighted element, cancelling any torque exerted on the cutting member 118 and/or drive shaft 110 when bending while drilling.

Figure 2:
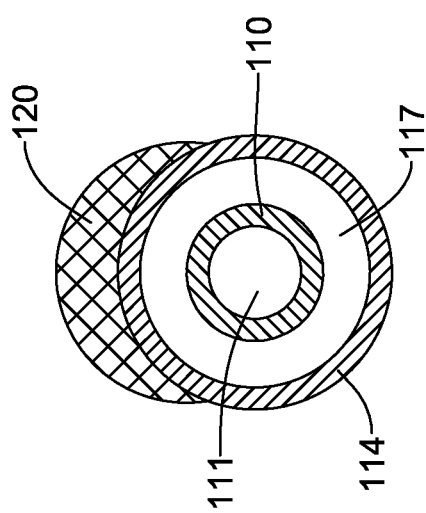
FIG. 2 is a cross-sectional view of the exemplary atherectomy device of FIG. 1 taken along the plane 2-2 depicted in FIG. 1.

Turning now to FIG. 2, a cross-sectional view of the exemplary atherectomy device 100 of FIG. 1 taken along the plane 2-2 of FIG. 1 is depicted. As shown, the second drive shaft 114 defining the second fluid lumen 117 may have the eccentric weight 120 eccentrically mounted on an outer surface 113 of the second drive shaft 114. Further, the first drive shaft 110 defining the first fluid lumen 111 may be rotatably disposed within the second fluid lumen 117 of the second drive shaft 114. In some instances, the first drive shaft 110 may also be axially translatable proximally and distally relative to the second drive shaft 114 to adjust the distance between the eccentric weight 120 and the cutting member 118, which may influence the vibrational movement of the cutting member 118 during operation of the device.

While attached to the distal end region 115 (as shown in FIG. 1), the eccentric weight 120 may partially cover the outer surface of the second drive shaft 114. However, it may be contemplated that the eccentric weight 120 may also completely surround the outer surface of the second drive shaft 114 with portions of the weight 120 unevenly distributed around the second drive shaft 114.

Figure 3:
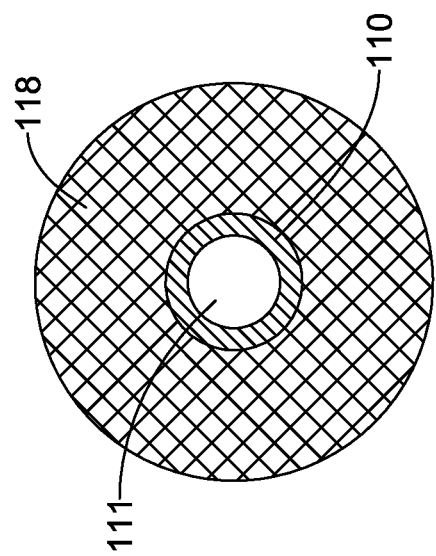
FIG. 3 is a cross-sectional view of the exemplary atherectomy device of FIG. 1 taken along the plane 3-3 depicted in FIG. 1.

FIG. 3 is a cross-sectional view of the exemplary atherectomy device 100 of FIG. 1 taken along the plane 3-3 of FIG. 1. As shown, the cutting member 118 may be attached to the first drive shaft 110. The cutting member 118 may be attached to the distal end region 109 (as shown in FIG. 1). As discussed previously, the cutting member 118 may remain concentric to the first drive shaft 110, or the cutting member 118 may be eccentrically positioned relative to the rotational axis of the first drive shaft 110. As illustrated, the cutting member 118 may completely surround an outer surface (not shown) of the first drive shaft 110.

Figure 4:
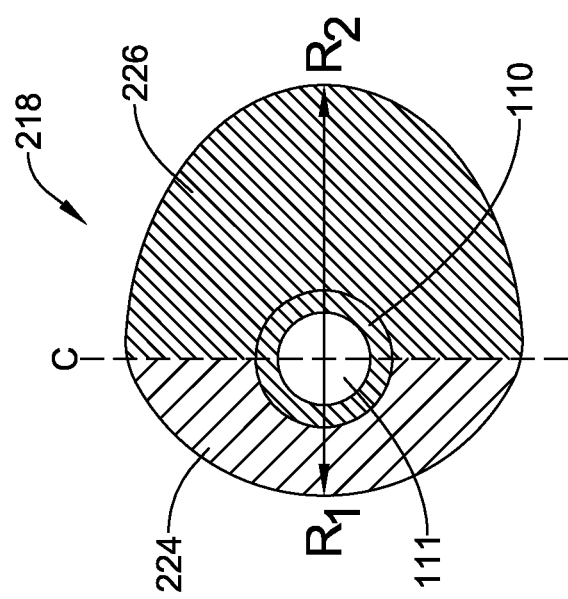
FIG. 4 is a transverse cross-sectional view of an exemplary cutting member of an atherectomy device.

FIG. 4 is a cross-sectional view of another cutting member 218 mounted on a drive shaft for use with an atherectomy device, such as the exemplary atherectomy device of FIG. 1 taken along the plane 3-3 of FIG. 1. In contrast to the above embodiments, the cutting member 218 in the illustrated embodiment may include a dual-density asymmetric configuration. More particularly, the cutting member 218 of the present embodiment may include a first portion 224 and a second portion 226 such that the mass density of the two portions 224 and 226 may vary. For instance, the mass density of the first portion 224 may be greater than the mass density of the second portion 226, or the mass density of the first portion 224 may be less than the mass density of the second portion 226. In addition, the two portions 224 and 226 may have an asymmetric configuration with a radius R1 of the first portion 224 from the central rotational axis of the first drive shaft 110 being smaller than a radius R2 of the second portion 226 from the central rotational axis of the first drive shaft 110.

It may be contemplated that the radius (R1 and R2) and the mass density of two portions (224, 226) may be such that the moment of inertia of the two portions (224, 226) may remain equal. For example, in an implementation where the radius R1 of the first portion 224 is greater than the radius R2 of the second portion 226, the mass density of the first portion 224 may be made less than the mass density of the second portion 226 to provide the same moment of inertia for both portions (224 and 226).

As a result, the cutting member 218 may be configured to rotate steadily around the first drive shaft 110, without vibration. However, different radii (R1, R2) of the two portions (224, 226) from the rotational axis of the first drive shaft 110 may facilitate formation of a larger hole through the occlusion on rotation of the cutting member 218. For instance, the diameter R1+R2 of the cutting member 218 at rest is less than the effective diameter of the rotating cutting member 218 (i.e., an effective diameter of 2×(R2)) and thus the diameter 2×(R2) of the opening which may be formed after drilling of an occlusion. Therefore, in such instances, the formed opening will have a diameter greater than the crossing profile of the cutting member 218.

In one embodiment, the two portions (224, 226) may be formed using molding techniques. Those skilled in the art will appreciate that the portions (224, 226) may be formed using any suitable technique including, but not limited to, casting, machining, or the like. The formed portions (224, 226) may be disposed around the first drive shaft 110 using suitable methods. Examples may include stamping, welding, press fit, swaging, or the like. These are some presented examples and should not be limiting the scope of the present disclosure.

In one embodiment, the two portions 224 and 226 may formed using two materials of different densities, which may provide the two portions (224 and 226) having different densities. Alternatively, the two portions 224 and 226 may be made from a similar material. In such instances, multiple micro-cavities or other voids may be formed in one portion to have the density of the other portion greater than the first portion. It may be contemplated that any suitable material may be employed to form the two portions. Examples may include, but are not limited to, metals, alloys, polymers, ceramics, composites, or the like. Further, the micro-cavities or other voids may be formed using any suitable technique known in to the art. Such techniques may include etching or laser treatment of either of the portions (224, 226), as well as casting or milling processes. Those skilled in the art will appreciate that such techniques are presented here as examples and thus should not be limiting the scope of the present disclosure.

Although not shown explicitly, the cutting member 218 may also formed of a single density symmetric structure. In such instances, the cutting member 218 may be eccentrically positioned relative to the rotational axis of the first drive shaft 110. More particularly, the cutting member 218 may be placed off-axis to the central rotational axis of the first drive shaft 110 and thus have a greater portion positioned to one side of a plane C parallel to and passing through the rotational axis than a portion positioned to the opposite side of the plane C. As a result, the opening created after boring through the occlusion may have a diameter larger than the actual profile (e.g., diameter) of the cutting member 218.

Figure 5:
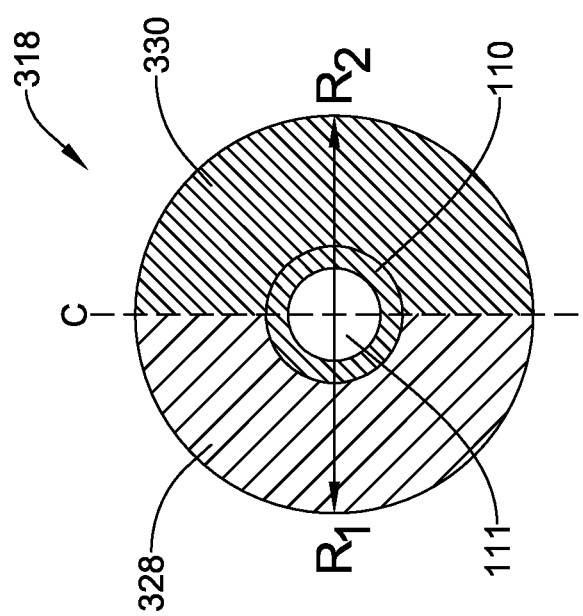
FIG. 5 is a transverse cross-sectional view of an exemplary cutting member of an atherectomy device.

Turning now to FIG. 5, a cross-sectional view of another cutting member 318 mounted on a drive shaft for use with an atherectomy device, such as the exemplary atherectomy device 100 of FIG. 1 taken along the plane 3-3 of FIG. 1 is depicted. In the illustrated embodiment, the cutting member 318 may define a symmetric structure, symmetrically positioned relative to the central rotational axis of the drive shaft 110 that may include two symmetric portions. The symmetric portions may include a first portion 328 and a second portion 330 such that a radius R1 of the first portion 328 is equal to the radius R2 of the second portion 330. In an implementation, the two portions (328, 330) may be attached to the distal end region 109 (as shown in FIG. 1) of the first drive shaft 110 to define a circular cross-section. However, those skilled in the art will appreciate that other suitable cross-sections may also be contemplated. Exemplary cross-sections may include oval, polygonal, irregular, or the like.

In the illustrated embodiment, the two portions (328, 330) may have different mass densities. For instance, the mass density of the first portion 328 may be less than the mass density of the second portion 330, or the mass density of the first portion 328 may be greater than the mass density of the second portion 330. As discussed previously, the variation in mass density of the two portions (328, 330) may be achieved either by using a different material to form each portion (328, 330) or by forming micro cavities or other voids in at least one portion to reduce its mass, for example. Those skilled it the art will appreciate that any suitable method may be contemplated to vary the mass density of the two portions (328, 330).

The difference in mass densities of the two portions (328, 330) may provide a different moment of inertia for the two portions (328, 330). Therefore, rotation of the drive shaft 110 may generate vibration of the cutting member 318, which may further facilitate formation of a larger opening through the occlusion. In particular, the opening formed may have a diameter greater than the overall diameter R1+R2 of the cutting member 318.

Figure 6:
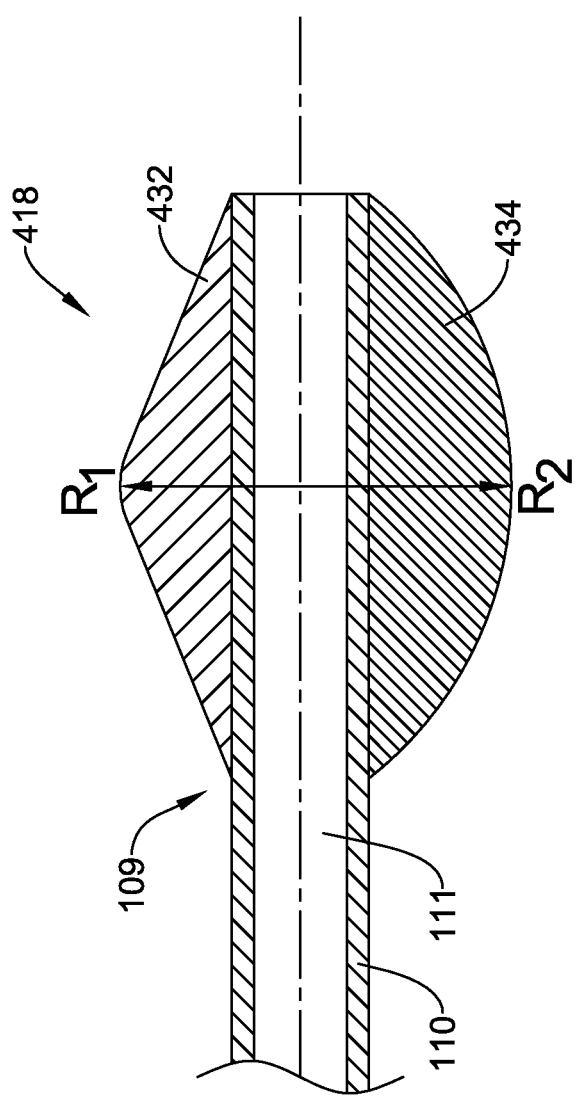
FIG. 6 is a longitudinal cross-sectional view of another embodiment of an exemplary cutting member of an atherectomy device.
Figure 7:
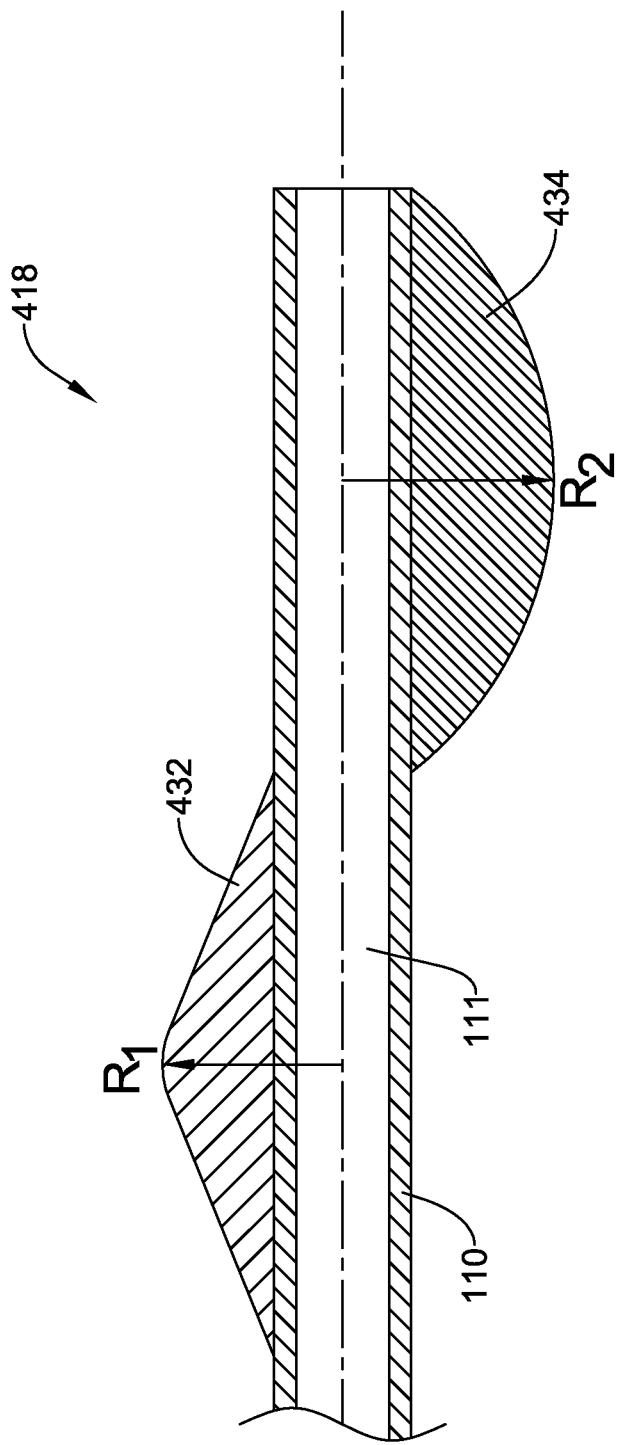
FIG. 7 is a longitudinal cross-sectional view of another embodiment of an exemplary cutting member of an atherectomy device.

Next, FIGS. 6-7 depict longitudinal cross-sectional views of further embodiments of a cutting member 418 mounted on a drive shaft for use with an atherectomy device, such as the exemplary atherectomy device of FIG. 1.

As shown in FIG. 6, the cutting member 418 may be disposed around the distal end region 109 of the first drive shaft 110. As discussed previously, the cutting member 418 may be formed of a first portion 432 and a second portion 434 such that the radius R1 of the first portion 432 is equal to the radius R2 of the second portion 434. In other instances, the radius R1 of the first portion 432 may be greater than or less than the radius R2 of the second portion 434. In such an embodiment, the mass of the two portions (432, 434) may vary. To accomplish this, the shape and/or configuration of the first portion 432 may differ from the second portion 434. For instance, in the illustrated embodiment, the first portion 432 may have a triangular shape while the second portion may have a substantially semi-circular configuration, although other shapes and/or configurations are possible. Further, the mass of the first portion 432 may be less than the mass of the second portion 434, therefore the moment of inertia of the two portions (432, 434) may vary. This may generate vibration of the cutting member 418 as the drive shaft is rotated at a desired speed, resulting in the formation of an opening through an occlusion larger than the profile (e.g., diameter) of the cutting member 418.

Further, the two portions (432, 434) may be attached to the first drive shaft 110 at various locations. For example, as shown in FIG. 6, the first portion 432 and the second portion 434 may be positioned at the same longitudinal position on the first drive shaft 110. Alternatively, as shown in FIG. 7, the two portions (432, 434) may be longitudinally offset from one other along the central axis of the first drive shaft 110, with the center of mass of the first portion 432 positioned on a first side of a plane parallel to and passing through the rotational axis and the center of mass of the second portion 434 positioned on a second, opposite side of a plane parallel to and passing through the rotational axis of the first drive shaft 110. In such implementation, the cutting member 418 may provide a sinusoidal cutting pattern with the first portion 432 moving in a first direction from the rotational axis as the second portion 434 is moving in a second direction from the rotational axis opposite the first direction. Such as configuration may generated desired vibratory characteristics of the cutting member 418, permitting a larger opening through an occlusion to be created. In such as configuration, the moment of inertia along the axis of the first drive shaft 110 may vary. In addition, the sinusoidal pattern of the two portions (432, 434) may provide drilling of an opening across a larger length.

Figure 8:
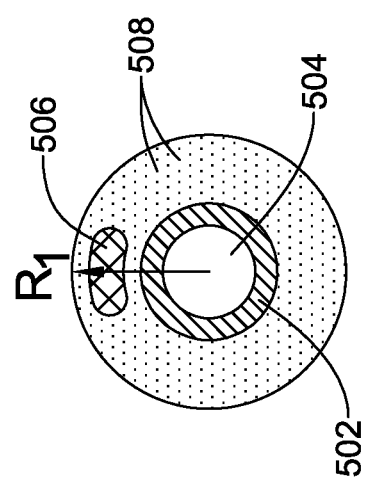
FIG. 8 is a transverse cross-sectional view of another embodiment of an exemplary cutting member of an atherectomy device s.

FIG. 8 is a cross-sectional view of another cutting device 500 mounted on a drive shaft 502 for use with an atherectomy device, such as the exemplary atherectomy device of FIG. 1 taken along the plane 3-3 of FIG. 1. As shown, the device 500 may include a rotatable drive shaft 502 having a lumen 504. While not shown explicitly, the lumen 504 may extend longitudinally from the distal end of the rotatable drive shaft 502 to at least a portion of the proximal end of the shaft 502 for passage of fluid and/or a medical device (e.g., guidewire) therethrough.

A cutting member 508 may be disposed on the rotatable drive shaft 502. More particularly, the cutting member 508 may be mounted on the rotatable drive shaft 502 defining a circular cross section. Other suitable cross-sections including, but not limited to, oval, irregular, or the like may also be contemplated. Here, in a stationary, non-rotating state, the cutting member 508 may have a radius R1 from the rotational axis of the drive shaft 502, which may be defined as the radius of the cutting member 508 during insertion into a vessel or a body cavity.

It may be contemplated that the cutting member 508 may be made form an elastically deformable material. Examples may include a flexible member made from a variety of biocompatible materials such as, but not limited to, elastomeric polymers, silicone, or the like.

In some embodiments, the cutting member 508 may also include an abrasive material. In some instances, the abrasive material may be disposed throughout the cross section of the elastically deformable cutting member 508. Alternatively, the abrasive material may be disposed partially to the cross-section of the elastically deformable cutting member 508. In some embodiments, the abrasive material may be coated around an outer surface of the elastically deformable cutting member 508. As previously discussed, the abrasive material may include diamond powder, fused silica, titanium nitride, tungsten carbide, aluminum oxide, boron carbide, or other ceramic materials, for example.

Further, a weight 506 may be disposed with the elastically deformable cutting member 508. For example, the weight 506 may be disposed on or within the elastically deformable cutting member 508. It may be contemplated that the mass density of the weight 506 may be larger than the mass density of the cutting member 508. The weight 506 may be asymmetrically or symmetrically positioned at one or more radial locations from the rotational axis. Rotation of the rotatable drive shaft 502 may allow rotation of the cutting member 508 at a corresponding rotational rate. At slower rotational rates, e.g., rotational rates below a threshold rotational rate, the elastically deformable cutting member 508 may not appreciably elastically deform. However, a further increase in the rotational rate above a threshold rate may allow radial elongation or expansion of the cutting member 508 away from the rotational axis (as shown in FIG. 9).

Figure 9:
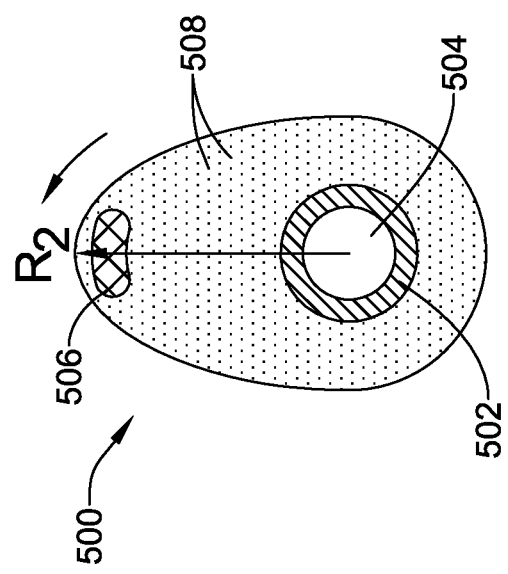
FIG. 9 is a transverse cross-sectional view of the cutting member of FIG. 8 being subjected to centrifugal forces.

FIG. 9 is a cross-sectional view of the cutting member 508 of FIG. 8 with the rotatable drive shaft 502 rotating at a speed above the threshold speed. In the illustrated embodiment, the rotatable drive shaft 502 may rotated at a speed above a threshold rotational rate, thus the centrifugal forces acting on the weight 506 may move the weight 506 radially away from the rotational axis to radially deform the cutting member 508. As a result, the cutting member 508 may be deformed radially outward such that a radius R2 of the cutting member 508 while rotating above a threshold rotational rate is greater than the radius R1 of the cutting member 508 at rest as well as at rotational rates below the threshold rotational rate. The cutting member 508 with radius R2 greater than the resting radius R1 will permit the formation of a larger diameter opening through an occlusion. It may be contemplated that the smaller resting diameter R1 may facilitate navigation of the cutting member 508 and drive shaft 502 through a vascular lumen to an occlusion; however, the larger cutting diameter R2 may permit the formation of a larger opening through the occlusion to revascularize the blood vessel.

Figure 10:
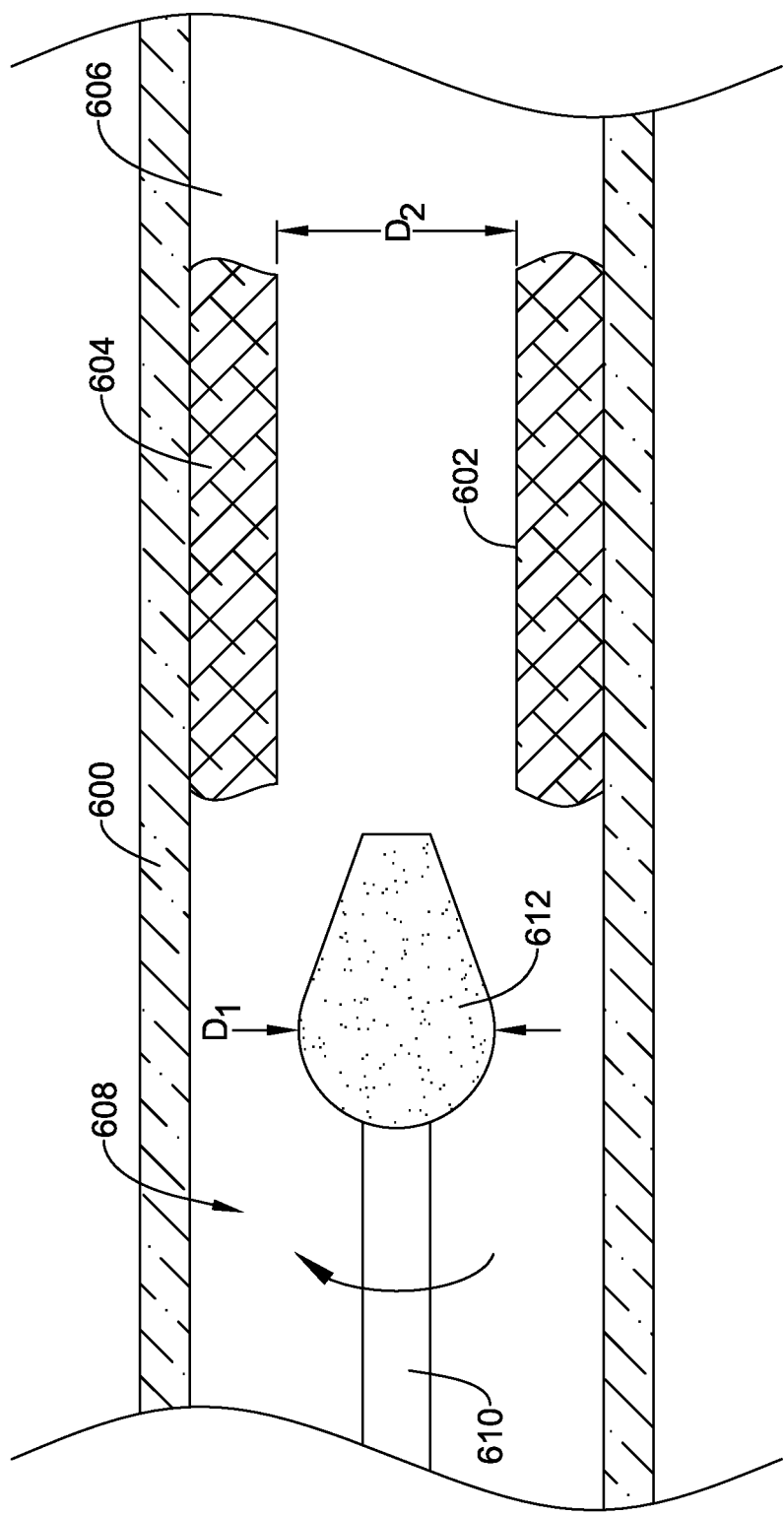
FIG. 10 illustrates an exemplary method for revascularization of an occluded blood vessel using the atherectomy device of FIG. 1.

FIG. 10 illustrates an exemplary implementation or use of an atherectomy device 608 (similar in function of device 100 of FIG. 1) for revascularization of an occluded blood vessel 600. Typically, the atherectomy device 608 is used to form an opening 602 through an occlusion 604 located in the blood vessel 600.

As shown, the atherectomy device 608 may include a rotatable cutting device 612, such as any of the cutting members described herein, attached to a distal end region of a first drive shaft 610. The first drive shaft 610 may be rotated while being advanced through the occlusion 604, thereby creating an opening 602 through the occlusion 604. The cutting member 612 may be configured to form an opening 602 having a diameter D2 greater than the diameter of the cutting member 612, as described herein. In some instances, the atherectomy device 608 may further include a second drive shaft (as shown in FIG. 1), which may be configured to rotate independent to the first drive shaft 610. The second drive shaft may have an eccentric weight 120 (as shown in FIG. 1) disposed at its distal end. The rotation of the second drive shaft above a threshold rotational rate generates vibration of the eccentric weight 120. As a result, the second drive shaft may induce vibrations in the first drive shaft 610 and thus the cutting member 612. Therefore, the rotatable cutting device 612 may experience a vibration, which may create a larger diameter opening 602 in the occlusion 604. Thus, in some instances, the cutting member 612 may be rotated while the second drive shaft is stationary to form an opening through the occlusion 604. When desired, rotation of the second drive shaft, and thus the weight, may be initiated to cause the cutting member 612 to begin to vibrate, thus enlarging the opening 602 through the occlusion 604. Thus, vibration of the cutting member 612 may be controlled by independently controlling rotation of the first and second drive shafts. The amount of vibration of the cutting member 612, and thus size of the opening 602, may be achieved by increasing or decreasing the rotational rate of the second drive shaft. For example, the user may increase the speed of the second drive shaft to increase the vibration of the cutting member 612, and thus increase the size of the opening 602 formed through the occlusion 604. It is contemplated that the larger cutting diameter is achieved with the cutting device 612 of relatively smaller profile, which thus makes the atherectomy procedure more efficient at remote or tortuous locations in the vasculature.

It is contemplated that the threshold rotational rate in the above embodiments may include any suitable rotations per minute (rpm) above which the cutting member starts vibrating. Exemplary rotational rates may include 2,000 rpm to 90,000 rpm. Those skilled in the art will appreciate that any suitable rotational rate may be employed to accomplish the desired operations.

Those skilled in the art will recognize the aspects of the present disclosure may be manifest in a variety of forms other than the specific embodiments described and contemplated herein. Accordingly, departure in form and detail may be made without departing from the scope and spirit of the present disclosure as described in the appended claims.

What is claimed is:

1. An atherectomy device comprising:
a handle assembly;
a first drive shaft extending distally from the handle assembly and having a cutting member mounted on a distal end region of the first drive shaft;
a second drive shaft extending distally from the handle assembly to a distal end of the second drive shaft;
wherein the first drive shaft extends through the second drive shaft;
wherein the handle assembly is configured to rotate the first drive shaft;
wherein the handle assembly is configured to rotate the second drive shaft independently of the first drive shaft.

2. The atherectomy device of claim 1, wherein the second drive shaft includes an eccentric weight such that rotation of the second drive shaft above a threshold rotational rate causes the cutting member mounted on the first drive shaft to vibrate.

3. The atherectomy device of claim 2, wherein the cutting member is configured to create an opening having a first diameter when the first drive shaft is rotating and the second drive shaft is rotating below the threshold rotational rate, and the cutting member is configured to create an opening having a second diameter greater than the first diameter when the first drive shaft is rotating and the second drive shaft is rotating above the threshold rotational rate.

4. The atherectomy device of claim 3 wherein the cutting member is concentrically mounted on the first drive shaft.

5. The atherectomy device of claim 1, wherein the first drive shaft extends through the second drive shaft such that the cutting member is positioned distal of the distal end of the second drive shaft.

6. The atherectomy device of claim 5, wherein a first fluid lumen is defined through a lumen of the first drive shaft and a second fluid lumen is defined between an inner surface of the second drive shaft and an outer surface of the first drive shaft.

7. The atherectomy device of claim 1, wherein the first drive shaft is rotatable in a first direction while the second drive shaft is rotatable in a second direction, opposite the first direction.

8. The atherectomy device of claim 1, wherein the cutting member is eccentrically positioned on the first drive shaft.

9. The atherectomy device of claim 8:
wherein a first portion of the cutting member is located on a first side of a plane passing through a rotational axis of the first drive shaft and a second portion of the cutting member is located on a second side of the plane passing through the rotational axis of the first drive shaft;
wherein the first portion has a first radius from the rotational axis and the second portion has a second radius from the rotational axis greater than the first radius;
wherein the first portion of the cutting member has a first moment of inertia and the second portion of the cutting member has a moment of inertia equal to the first moment of inertia; and
wherein the first portion of the cutting member has a density and the second portion of the cutting member has a density less than the density of the first portion.

10. The atherectomy device of claim 1, wherein the handle assembly includes a first motor for controlling rotational movement of the first drive shaft and a second motor for controlling rotational movement of the second drive shaft.

11. The atherectomy device of claim 1, further comprising a motor for controlling rotational movement of the first and second drive shafts.

12. The atherectomy device of claim 11, further comprising a clutch for selectively engaging and disengaging rotational movement of the second drive shaft.

13. A method of forming an opening through an occlusion in a blood vessel, comprising:
advancing a cutting member of a rotatable cutting device to a location proximate an occlusion, the cutting device including:
a handle assembly;
a first drive shaft extending distally from the handle assembly, the cutting member mounted to the first drive shaft;
a second drive shaft extending distally from the handle assembly, wherein the first drive shaft extends through the second drive shaft;
rotating the first drive shaft while advancing the cutting member through the occlusion; and
rotating the second drive shaft independently of the first drive shaft to initiate vibration of the cutting member while advancing the cutting member through the occlusion.

14. The method of claim 13, wherein the rotatable cutting device includes an eccentric weight mounted on a distal end region of the second drive shaft.

15. The method of claim 13, wherein the rotatable cutting device is configured to control rotation of the second drive shaft independent of rotation of the first drive shaft.

* * * * *